United States Patent
Krans et al.

(10) Patent No.: US 10,531,954 B2
(45) Date of Patent: Jan. 14, 2020

(54) MITRAL VALVE LOADING TOOL

(71) Applicant: St. Jude Medical, Cardiology Division, Inc., St. Paul, MN (US)

(72) Inventors: Mark Krans, Hopkins, MN (US); Theodore Paul Dale, Corcoran, MN (US); Andrea N. Para, St. Louis, MO (US); Mathias Charles Glimsdale, St. Michael, MN (US); Thomas M. Benson, Minneapolis, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 278 days.

(21) Appl. No.: 15/072,728

(22) Filed: Mar. 17, 2016

(65) Prior Publication Data
US 2016/0270914 A1    Sep. 22, 2016

Related U.S. Application Data

(60) Provisional application No. 62/135,921, filed on Mar. 20, 2015.

(51) Int. Cl.
| | | |
|---|---|---|
| *A61F 2/24* | (2006.01) | |
| *A61F 2/95* | (2013.01) | |
| *A61F 2/966* | (2013.01) | |

(52) U.S. Cl.
CPC .......... *A61F 2/2436* (2013.01); *A61F 2/2418* (2013.01); *A61F 2/95* (2013.01); *A61F 2002/9522* (2013.01); *A61F 2002/9665* (2013.01)

(58) Field of Classification Search
CPC ............ A61F 2/2436; A61F 2002/9522; A61F 2002/9665; A61F 2/95; A61F 2/2418
See application file for complete search history.

(56) References Cited

U.S. PATENT DOCUMENTS 5,891,193 A * 4/1999 Robinson .................. A61F 2/07
                                                        128/898
6,132,458 A * 10/2000 Staehle ................. A61F 2/0095
                                                        623/1.11
(Continued)

FOREIGN PATENT DOCUMENTS

| EP | 0657147 A2 | 6/1995 |
|---|---|---|
| WO | 2011150399 A1 | 12/2011 |

(Continued)

OTHER PUBLICATIONS

International Search Report for Application No. PCT/US2016/022748 dated Aug. 8, 2016.

(Continued)

*Primary Examiner* — Jing Rui Ou
(74) *Attorney, Agent, or Firm* — Lerner, David, Littenberg, Krumholz & Mentlik, LLP

(57) ABSTRACT

A loading tool for loading a collapsible prosthetic heart valve into a delivery device may include a body extending in a longitudinal direction between a proximal end and a distal end, an extension on the distal end of the body, and a slot extending through the extension from a free end of the extension toward the distal end of the body. The body may include a lumen extending between the proximal end and the distal end, the body lumen having a first diameter. The extension may have a lumen coaxial with the body lumen, the extension lumen having a second diameter less than the first diameter so as to define a shelf surface between the proximal end of the body and the free end of the extension.

11 Claims, 6 Drawing Sheets

(56) References Cited

U.S. PATENT DOCUMENTS

| | | | |
|---|---|---|---|
| 6,395,017 B1* | 5/2002 | Dwyer | A61F 2/962 623/1.11 |
| 9,192,469 B2* | 11/2015 | Mearns | A61F 2/2412 |
| 2002/0120323 A1* | 8/2002 | Thompson | A61F 2/91 623/1.11 |
| 2004/0127912 A1 | 7/2004 | Rabkin et al. | |
| 2005/0137692 A1 | 6/2005 | Haug et al. | |
| 2005/0182486 A1* | 8/2005 | Gabbay | A61F 2/2409 623/2.11 |
| 2006/0259135 A1 | 11/2006 | Navia et al. | |
| 2006/0287718 A1* | 12/2006 | Bicer | A61F 2/2418 623/2.11 |
| 2007/0162107 A1 | 7/2007 | Haug et al. | |
| 2007/0239271 A1* | 10/2007 | Nguyen | A61F 2/2436 623/2.11 |
| 2008/0071363 A1 | 3/2008 | Tuval et al. | |
| 2009/0054976 A1* | 2/2009 | Tuval | A61F 2/0095 623/2.11 |
| 2009/0099530 A1* | 4/2009 | Adams | A61F 2/95 604/264 |
| 2010/0057185 A1* | 3/2010 | Melsheimer | A61F 2/95 623/1.12 |
| 2010/0121434 A1 | 5/2010 | Paul et al. | |
| 2010/0262231 A1 | 10/2010 | Tuval et al. | |
| 2010/0312333 A1 | 12/2010 | Navia et al. | |
| 2011/0295216 A1* | 12/2011 | Miller | A61F 2/2436 604/264 |
| 2012/0083874 A1* | 4/2012 | Dale | A61F 2/2427 623/2.11 |
| 2013/0274870 A1 | 10/2013 | Lombardi et al. | |
| 2013/0297011 A1 | 11/2013 | Morris et al. | |
| 2014/0046428 A1 | 2/2014 | Cragg et al. | |
| 2014/0371844 A1 | 12/2014 | Dale et al. | |
| 2017/0165064 A1 | 6/2017 | Nyuli et al. | |

FOREIGN PATENT DOCUMENTS

| | | |
|---|---|---|
| WO | 2012127309 A1 | 9/2012 |
| WO | 2012178115 A2 | 12/2012 |
| WO | 2013028387 A2 | 2/2013 |
| WO | 2013059747 A1 | 4/2013 |

OTHER PUBLICATIONS

International Search Report and Written Opinion for Application No. PCT/US2014/042914 dated Nov. 14, 2014.
Partial International Search Report for Application No. PCT/US2014/042914 dated Oct. 21, 2014.
European Search Report for EP Application No. 18195359.7, dated Jan. 22, 2019.

* cited by examiner

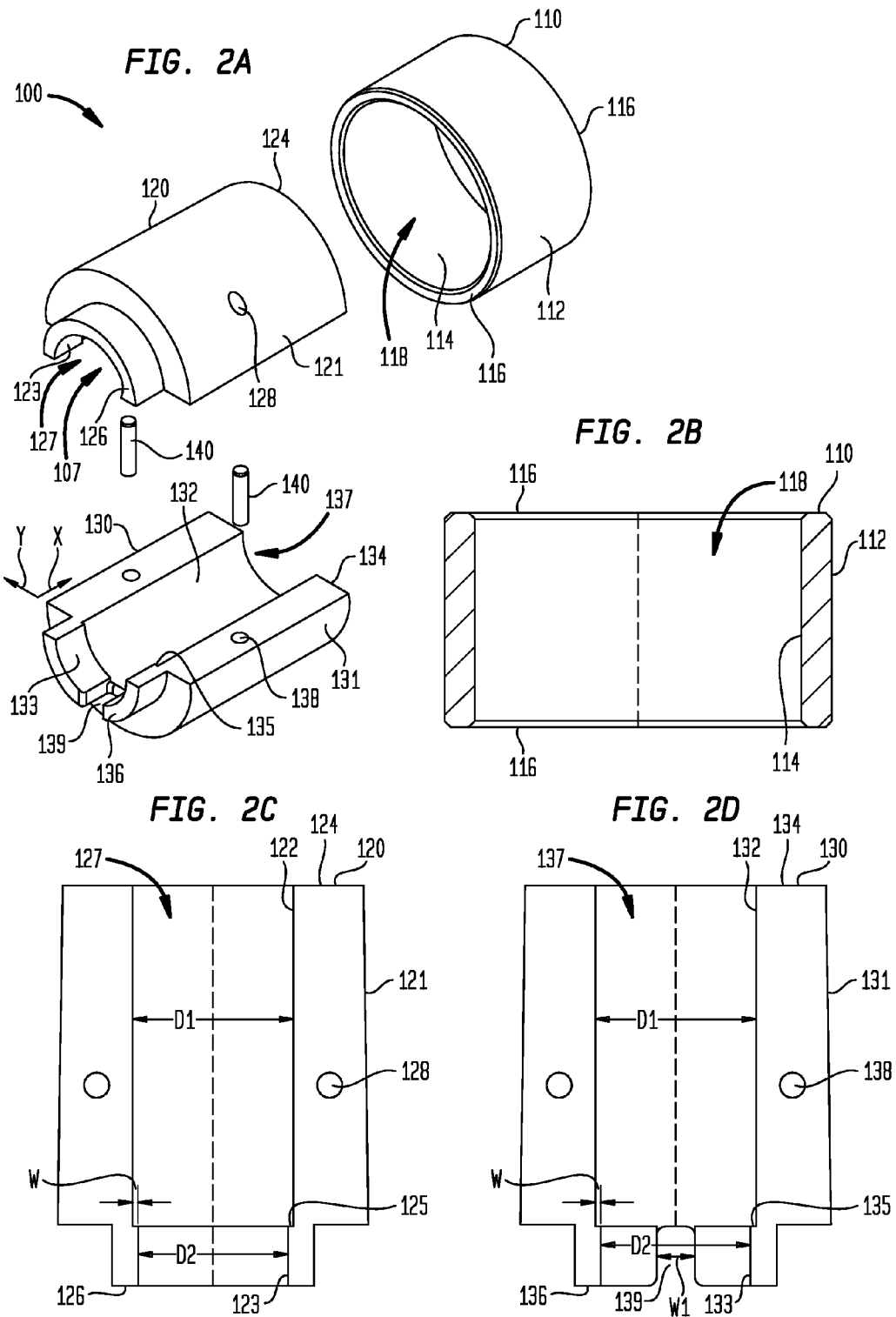

MITRAL VALVE LOADING TOOL

CROSS-REFERENCE TO RELATED APPLICATIONS

This application claims the benefit of the filing date of U.S. Provisional Patent Application No. 62/135,921, filed Mar. 20, 2015, the disclosure of which is hereby incorporated herein by reference.

BACKGROUND OF THE INVENTION

The present disclosure relates to heart valve replacement and, in particular, to the delivery of collapsible prosthetic heart valves. More particularly, the present disclosure relates to devices and methods for delivering collapsible prosthetic heart valves within native valve annuluses.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

Described herein is a loading tool for loading a collapsible prosthetic heart valve into a delivery device. The loading tool may include a body extending in a longitudinal direction between a proximal end and a distal end, the body including a lumen extending between the proximal end and the distal end, the body lumen having a first diameter. The loading tool may also include an extension on the distal end of the body, the extension having a free end and a lumen coaxial with the body lumen, the extension lumen having a second diameter less than the first diameter so as to define a shelf surface between the proximal end of the body and the free end of the extension. The loading tool may further include a slot extending through the extension from the free end toward the distal end of the body.

Also described herein is medical combination. The medical combination may include a delivery device for a collapsible prosthetic heart valve. The delivery device may include an inner sheath elongated along a longitudinal axis. The delivery device may also include an outer sheath at least partially surrounding the inner sheath and slidable relative to the inner sheath along the longitudinal axis, the outer sheath having a first diameter. The delivery device may further include a retaining element affixed to the inner sheath, the retaining element having a plurality of recesses distributed circumferentially around its perimeter, each recess being configured to accept a corresponding retainer of the prosthetic heart valve, the perimeter of the retaining element having a second diameter.

The medical combination may also include a loading tool for loading the collapsible prosthetic heart valve into the delivery device. The loading tool may include a body extending in a longitudinal direction between a proximal end and a distal end, the body including a lumen extending between the proximal end and the distal end, the body lumen having a third diameter greater than the first diameter so that the outer sheath fits within the body lumen when the loading tool is in an assembled condition around the delivery device. The loading tool may also include an extension on the distal end of the body, the extension having a free end and a lumen coaxial with the body lumen, the extension lumen having a fourth diameter less than the third diameter so as to define a shelf surface between the proximal end of the body and the free end of the extension, the fourth diameter being greater than the second diameter so that the retaining element fits within the extension lumen when the loading tool is the assembled condition around the delivery device. The loading tool may further include a slot extending through the extension from the free end toward the distal end of the body.

Also described herein is a method of loading a collapsible prosthetic heart valve into a delivery system. The method may include assembling a loading tool around a distal end of a delivery device for a collapsible prosthetic heart valve. The delivery device may have a retaining element and an outer sheath elongated along a longitudinal axis and slidable relative to the retaining element along the longitudinal axis, the retaining element having a plurality of recesses distributed circumferentially around its perimeter.

The loading tool may have a body and an extension on the distal end of the body, the body extending in a longitudinal direction between a proximal end and a distal end and including a lumen extending between the proximal end and the distal end, the extension having a free end and a lumen coaxial with the body lumen, the extension lumen defining a shelf surface between the proximal end of the body and the free end of the extension, the loading tool having a slot extending through the extension from the free end toward the distal end of the body.

The method may also include placing a first retainer of a collapsible prosthetic heart valve through the slot and into a corresponding first one of the recesses of the retaining element, and rotating the loading tool about the longitudinal axis until a second one of the recesses of the retaining element is exposed within the slot. The method may further include placing a second retainer of the collapsible prosthetic heart valve through the slot and into a corresponding second one of the recesses of the retaining element, and rotating the loading tool about the longitudinal axis until the first one and the second one of the recesses are not exposed within the slot. The method may also include advancing the outer sheath relative to the retaining element along the longitudinal axis, so that the outer sheath covers the first one and the second one of the recesses, and removing the loading tool from the distal end of the delivery device.

Also described herein is a delivery device for a collapsible prosthetic heart valve. The delivery device may include an inner shaft elongated along a longitudinal axis, and an inner sheath at least partially surrounding the inner sheath and slidable relative to the inner sheath along the longitudinal axis. The delivery device may also include a retaining element affixed to the inner sheath, the retaining element having a plurality of recesses distributed circumferentially around its perimeter, each recess being configured to accept a corresponding retainer of the prosthetic heart valve.

The delivery device may further include an outer sheath including a proximal segment and a distal segment that together define a compartment sized to receive the prosthetic heart valve therein, each of the proximal segment and the distal segment being independently slidable relative to the retaining element along the longitudinal axis. The delivery device may also include an atraumatic tip affixed to a distal end of the distal segment, the atraumatic tip having a distal end, a proximal end, and a recess open towards an interior of the distal segment, the recess sized to receive an end of the prosthetic heart valve therein in a collapsed condition.

Also described herein is another delivery device for a collapsible prosthetic heart valve. The delivery device may include an inner shaft extending in a longitudinal direction, and an inner sheath at least partially surrounding the inner sheath and slidable relative to the inner sheath in the longitudinal direction. The delivery device may also include a retaining element affixed to the inner sheath, the retaining element having a plurality of recesses distributed circumferentially around its perimeter, each recess being configured to accept a corresponding retainer of the prosthetic heart valve.

The delivery device may further include an outer sheath including a proximal segment and a distal segment that together define a compartment sized to receive the prosthetic heart valve therein, each of the proximal segment and the distal segment being independently slidable relative to the retaining element in the longitudinal direction, and a radiopaque marker on at least one of the proximal segment and the distal segment.

BRIEF DESCRIPTION OF THE DRAWINGS

Various embodiments of the present disclosure are disclosed herein with reference to the drawings, wherein:

FIG. 2A is an exploded perspective view of a loading tool configured to load the prosthetic heart valve of FIG. 1D into the delivery device of FIG. 1A;

FIG. 2B is a longitudinal cross-section of the ring of the loading tool of FIG. 2A;

FIG. 2C is a side view of the closed segment of the loading tool of FIG. 2A;

FIG. 2D is a side view of the open segment of the loading tool of FIG. 2A;

DETAILED DESCRIPTION

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user using the device in an intended manner "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

Figure 1A:
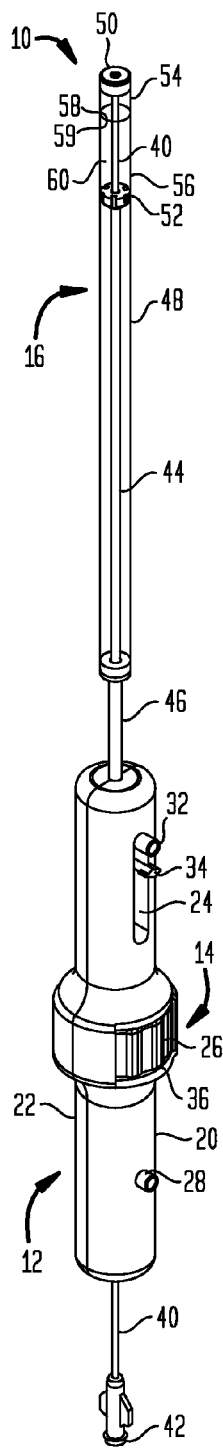
FIG. 1A is a perspective view of a delivery device with an outer sheath being shown as partially transparent.

Referring now to FIG. 1A, an exemplary delivery device 10 for use in delivering a collapsible prosthetic heart valve (or other types of self-expanding collapsible stents) is shown. Generally, the delivery device 10 includes a handle 12, an actuator 14, and a catheter assembly 16. The catheter assembly 16, which is illustrated as partially transparent in FIG. 1A, may function to deliver the prosthetic heart valve to and deploy the heart valve at a target location. The actuator 14 may function to control deployment of the valve from the catheter assembly 16. The handle 12 may function to facilitate operation of the other components by a user. Each of these components is described in greater detail below. An exemplary method of use of the delivery device 10 and further structural details thereof are shown and described in the co-owned and co-pending U.S. Patent Application Publication No. 2014/0371844, the disclosure of which is hereby incorporated herein by reference.

As illustrated in FIG. 1A, handle 12 includes a top portion 20 and a bottom portion 22. The top and bottom portions 20 and 22 may be individual pieces configured to be joined to one another as shown in FIG. 1A. For example, the top and bottom portions 20 and 22 may include some combination of mating features, such as pegs and corresponding holes, to facilitate connecting the top and bottom portions together.

The top and bottom portions 20 and 22 may be connected to one another in any other suitable manner, including, for example, by fasteners or an adhesive.

The top and bottom portions 20 and 22, individually or collectively, define a number of spaces to house components of actuator 14 and catheter assembly 16. For example, the top and bottom portions 20 and 22 define an elongated space in the handle 12 in which a lead screw 30 (FIG. 1B) is positioned and through which the lead screw may translate. The top portion 20 may also include an elongated window 24 through which a flush port 32 and a stop member 34 may extend. Similarly, the top and bottom portions 20 and 22 may define a generally circular or cylindrical space 26 in which a knob 36 is positioned. Finally, the top portion 20 may include a flush aperture 28 sized to receive a flush port on a flush adapter 38 of the catheter assembly 16.

An inner shaft 40 of the catheter assembly 16 is also illustrated in FIG. 1A. It should be appreciated that, although some components of the catheter assembly 16 are illustrated in FIG. 1A, others are omitted for purposes of clarity. The inner shaft 40 may extend from beyond a proximal end of the handle 12, through the handle subassembly, to a distal portion of delivery device 10 (the distal portion is described in greater detail below with reference to FIG. 1C). In particular, the inner shaft 40 may extend through correspondingly shaped bores through the lead screw 30 and the flush adapter 38, and to a proximal hub 42.

The proximal hub 42 may be positioned proximally of the proximal end of handle 12 such that, during use, a user may grasp the proximal hub. The fit between the inner shaft 40 and the through bores of the lead screw 30 and the flush adapter 38 is preferably snug enough to keep the inner shaft in place until the user applies intentional force to the inner shaft, for example by manually pushing or pulling the proximal hub 42 distally or proximally.

The knob 36 may have a textured cylindrical surface, such as a plurality of spaced ridges, to assist the user in gripping and rotating the knob. The lead screw 30 extends into a central aperture in the knob 36. The central aperture in the knob 36 may be internally threaded and configured to mate with external threads on lead screw 30. As the knob 36 is longitudinally confined within the space 26, rotation of the knob causes the lead screw 30 to translate proximally or distally depending on the direction of rotation.

The flush port 32 and the stop member 34 may be affixed to the lead screw 30. The engagement of the stop member 34 in the elongated window 24 prevents the lead screw 30 from simply rotating with the knob 36 and keeps the lead screw aligned in the longitudinal direction of the handle 12. The stop member 34 may further provide a limit on the distance that the lead screw 30 may translate proximally within the handle 12. The flush port 32 may provide a limit on the distance that the lead screw 30 may translate distally within the handle 12.

Figure 1B:
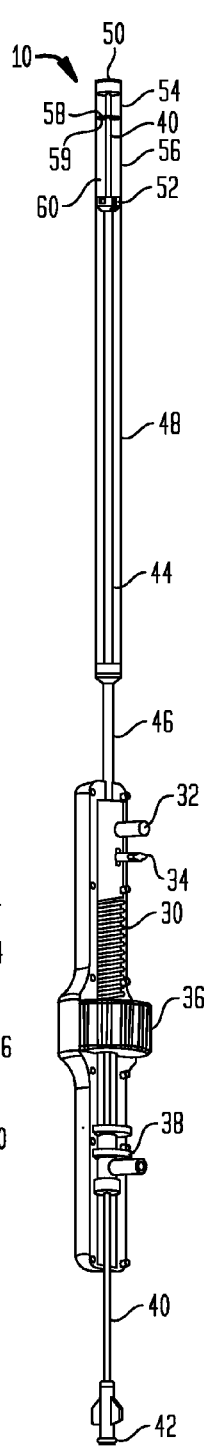
FIG. 1B is a perspective view of the delivery device of FIG. 1A with a portion of the handle subassembly removed.

FIG. 1B best illustrates the components of the catheter assembly 16, with the top portion 20 of the handle 12 removed. In general, the catheter assembly 16 includes the inner shaft 40, described in part above in relation to FIG. 1A, an inner sheath 44, a middle sheath 46, and an outer sheath 48, shown in FIG. 1B as partially transparent. The inner shaft 40 extends from the proximal hub 42 to an atraumatic distal tip 50, described more fully below. The outer sheath 48 may have a distal segment 54 and a proximal segment 56, described more fully below.

The inner sheath 44 is positioned over the inner shaft 40 and extends from the flush adapter 38, through the knob 36 and the lead screw 30, and terminates at a retaining element 52. The inner sheath 44 is axially fixed with respect to the handle 12 due, at least in part, to its connection to the flush adapter 38, which is held in a fixed axial position by ribs (not shown) of the top and bottom portions 20 and 22 of the handle 12.

The middle sheath 46 is positioned over the inner sheath 44 and the inner shaft 40, and extends from the distal end of the lead screw 30 to the proximal end of the outer sheath 48. The middle sheath 46 is connected to both the lead screw 30 and the proximal end of the outer sheath 48 such that proximal or distal translation of the lead screw causes corresponding translation of the middle sheath as well as the portion of the outer sheath to which the middle sheath is connected.

The outer sheath 48 is positioned over the inner sheath 44 and the inner shaft 40, and extends from the distal end of the middle sheath 46 to the atraumatic distal tip 50. The distal portion of the outer sheath 48 is illustrated in greater detail in FIG. 1C, again with the outer sheath being illustrated as partially transparent. The distal tip 50 may be blunt to facilitate advancement of the delivery device 10 without injury to the patient's tissue. For example, the distal tip 50 may have a substantially flat distal surface that is substantially perpendicular to the longitudinal axis of the outer sheath 48.

Figure 1C:
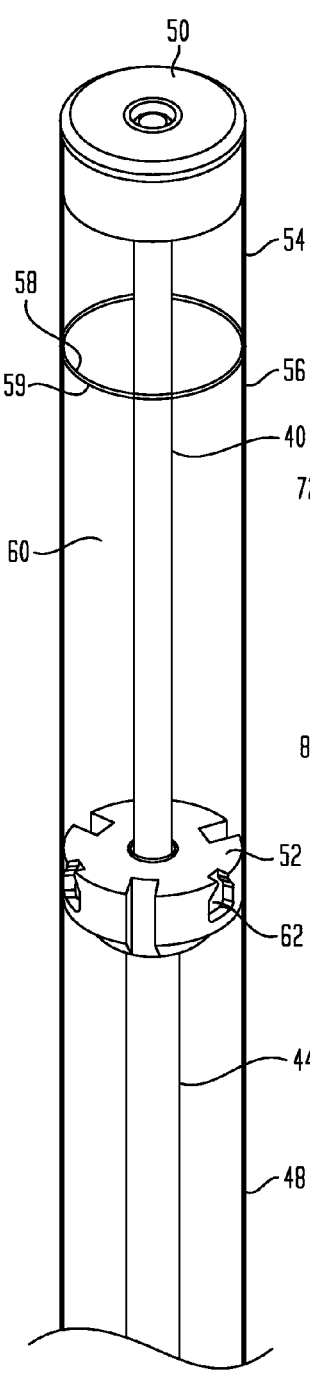
FIG. 1C is a perspective view of a distal portion of the delivery device of FIG. 1A shown as partially transparent.

The configuration of the distal tip 50 shown in FIG. 1C may be particularly suited for use in delivering a prosthetic valve transapically to a native mitral valve annulus. This is because, during transapical mitral valve delivery, for example, the prosthetic valve typically is deployed by moving the distal segment 54 of the outer sheath 48 distally, away from the proximal segment 56 of the outer sheath. However, there may be relatively little working space for the distal segment 54 of the outer sheath 48 to move in a distal direction. If the distal segment 54 of the outer sheath 48 extends too far distally during deployment of a prosthetic heart valve from the delivery device 10, tissue in the left atrium may be damaged.

The distal tip 50, with its atraumatic and blunted design, may help mitigate the risk of damaging native tissue during valve delivery and may maximize the working space available for the outer sheath 48 to open. This concern may be less evident during transapical aortic valve delivery, in which the distal tip 50 may be able to extend into the aortic arch during deployment of a prosthetic heart valve from delivery device 10, thus providing additional space for the distal tip to extend in a distal direction before contacting native tissue.

The outer sheath 48 may have a distal segment 54 and a proximal segment 56. The distal segment 54 may be coupled to the distal tip 50 so that movement of the inner shaft 40 (for example, by a user grasping and moving the proximal hub 42) results in a corresponding movement of the distal segment. The proximal segment 56 may be coupled to the middle sheath 46, which in turn is coupled to the lead screw 30, so that movement of the middle sheath (for example, by a user rotating the knob 36) results in a corresponding movement of the proximal segment. The distal segment 54 and the proximal segment 56 may include complementary releasable coupling features such as ribs, clips or fasteners for ensuring that they do not become separated from one another during delivery of a prosthetic valve into a patient. In one example, the proximal end 58 of the distal segment 54 may be slightly smaller in diameter than the distal end 59 of the proximal segment 56 such that these ends may mate with one another in an overlapping friction fit relationship.

The space between the retaining element 52 and the distal tip 50 defines a compartment 60 for housing a prosthetic heart valve. Specifically, a prosthetic heart valve may be disposed about inner shaft 40 in the compartment 60 and covered by the outer sheath 48. The retaining element 52 may include a plurality of recesses 62 distributed circumferentially around its perimeter, the recesses being configured to accept retainers disposed near the outflow end of the prosthetic heart valve, as will be described in more detail below. The distal segment 54 and the proximal segment 56 of the outer sheath 48 may be translatable relative to one another to form an increasing gap 64 therebetween (FIG. 1D) so as to expose the prosthetic heart valve in the compartment 60 for deployment. Further description of the aforementioned structural details of the delivery device 10 is provided in the co-owned and co-pending U.S. Patent Application Publication No. 2014/0371844, the disclosure of which is hereby incorporated herein by reference.

Figure 1D:
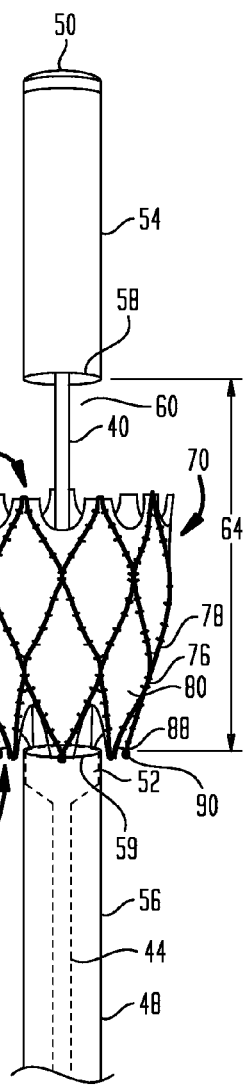
FIG. 1D is a schematic side view of a prosthetic heart valve that has been released by the delivery device of FIG. 1A.

FIG. 1D shows a collapsible prosthetic heart valve 70 in an expanded condition after being released from the compartment 60 of delivery device 10 by the distal movement of the distal segment 54 of the outer sheath 48 relative to the prosthetic heart valve and/or the proximal movement of the proximal segment 56 of the outer sheath relative to the prosthetic heart valve.

The collapsible prosthetic heart valve 70 is designed to replace the function of the native mitral valve of a patient. The prosthetic heart valve 70 has an inflow end 72 and an outflow end 74. The prosthetic heart valve 70 may be generally cylindrically shaped in the expanded condition and may include features for anchoring to native heart tissue, as will be discussed in more detail below. When used to replace a native mitral valve, the prosthetic heart valve 70 may have a low profile so as not to interfere with atrial function in the native valve annulus. Throughout this disclosure, a prosthetic heart valve 70 is used as an exemplary valve to be loaded into a delivery device such as the delivery device 10. However, the loading tool 100 that will be described below (FIGS. 2A through 4B) may be used to load any collapsible valve (e.g., a collapsible prosthetic aortic valve) or any collapsible stent having retainers into any delivery device having recesses distributed in a circumferential direction about a longitudinal axis of the delivery device.

The prosthetic heart valve 70 may include a stent 76, which may be formed from biocompatible materials that are capable of self-expansion, such as, for example, shape-memory alloys including Nitinol. The stent 76 may include a plurality of struts 78 that form closed cells 80 connected to one another in one or more annular rows around the stent. The cells 80 may all be of substantially the same size around the perimeter and along the length of the stent 76. Alternatively, the cells 80 near the inflow end 72 of the prosthetic valve 70 may be larger than the cells near the outflow end 74 of the valve. The stent 76 may be expandable to provide a radial force to assist with positioning and stabilizing the prosthetic heart valve 70 within the native mitral valve annulus of a patient.

The prosthetic heart valve 70 may also include a valve assembly disposed within the stent 76. The valve assembly may include a pair of leaflets (not shown) attached to a cylindrical cuff 82. The leaflets may replace the function of the native mitral valve leaflets of the patient. That is, the leaflets coapt with one another to function as a one-way valve. The prosthetic heart valve 70 may have more than two leaflets when used to replace the mitral valve or other cardiac valves within a patient. The valve assembly of the prosthetic heart valve 70 may be substantially cylindrical in the expanded condition. Both the cuff 82 and the leaflets may be wholly or partly formed of any suitable biological material, such as bovine or porcine pericardium, or polymers, such as polytetrafluoroethylene (PTFE), urethanes and the like.

When used to replace a native mitral valve, the valve assembly may be sized in the range of about 20 mm to about 40 mm in diameter. The valve assembly may be secured within the interior of the stent 76 by suturing to the struts 78 or by using tissue glue, ultrasonic welding, or other suitable attachment methods.

The prosthetic heart valve 70 may also include a number of retainers 90 disposed on the outflow end 74 of the prosthetic heart valve extending from certain junctions 88 of adjacent struts 78 of the stent 76. The retention of the retainers 90 in the recesses 62 of the retaining element 52 prevents the outflow end 74 of the prosthetic heart valve 70 from being inadvertently or unintentionally deployed from the proximal segment 56 of the outer sheath 48. During the deployment of the prosthetic heart valve 70 from the compartment 60, a user may rotate the knob 36, thereby moving the lead screw 30, the middle sheath 46, and the proximal segment 56 of the outer sheath 48 in a proximal direction. This proximal movement of the proximal segment 56 relative to the prosthetic heart valve 70 exposes the retainers 90 and allows them to disengage from the recesses 62 of the retaining element 52. Once disengaged from the retaining element 52, the prosthetic heart valve 70 may fully deploy into the patient.

FIGS. 2A-2D illustrate a loading tool 100 configured to load the prosthetic heart valve 70 into the delivery device 10. The loading tool 100 includes a clamp in the form of a ring 110, a first segment or closed segment 120 and a second segment or open segment 130 that together form a generally cylindrical body having an extension extending therefrom, and an alignment feature in the form of alignment pins 140 configured to align the positions of the closed and open segments relative to one another.

As shown in the figures herein, the closed segment 120 and the open segment 130 are identical except that the open segment has a opening in the form of a slot 139 formed therein, which will be described in detail below. The ring 110, the closed segment 120, the open segment 130, and the alignment pins 140 each may be made of a metal such as aluminum, for example, or any other rigid material or combination of materials, such as plastic, glass, or carbon fiber, among others.

As can be seen in FIG. 2B, the ring 110 may have a continuous outer surface 112 and a continuous inner surface 114 opposite the outer surface. The outer surface 112 and the inner surface 114 may each extend between opposed edge surfaces 116, and the inner surface may define a generally cylindrical lumen 118 that extends between the opposed edge surfaces. The ring is configured to snugly fit around the closed segment 120 and the open segment 130 in an assembled relationship, so that the closed segment and the open segment remain coupled to one another during use of the loading tool 100.

As shown in FIG. 2C, the closed segment 120 may have an outer surface 121, a proximal inner surface 122 opposite a proximal portion of the outer surface, and a distal inner surface 123 opposite a distal portion of the outer surface. The proximal inner surface 122 extends between a proximal edge 124 of the closed segment 120 and a shelf 125, and the distal inner surface 123 extends between the shelf and a distal edge 126 of the closed segment. The shelf 125 may have a half-ring shape and may face in a direction toward the proximal edge 124. The proximal inner surface 122 and the distal inner surface 123 together form a lumen 127 that extends between the proximal edge 124 and the distal edge 126. The closed segment 120 may also have two bores 128 that are each configured to receive a portion of an alignment pin 140 therein.

As shown in FIG. 2D, the open segment 130 may have an outer surface 131, a proximal inner surface 132 opposite a proximal portion of the outer surface, and a distal inner surface 133 opposite a distal portion of the outer surface. The proximal inner surface 132 extends between a proximal edge 134 of the closed segment 130 and a shelf 135, and the distal inner surface 133 extends between the shelf and a distal edge 136 of the closed segment. The shelf 135 may have a half-ring shape and may face in a direction toward the proximal edge 134. The proximal inner surface 132 and the distal inner surface 133 together form a lumen 137 that extends between the proximal edge 134 and the distal edge 136. The open segment 130 may also have two bores 138 that are each configured to receive a portion of an alignment pin 140 therein.

A slot 139 may extend between the outer surface 131 and the distal inner surface 133. The slot 139 may have an open side at the distal edge 136 and a closed side opposite the open side and may extend in a direction towards the shelf 125. The slot may have a width W1 greater than a width W2 of the retainers 90 of the prosthetic heart valve 70 (FIG. 3C).

The closed segment 120 and the open segment 130 may be assembled to one another (FIGS. 3B-3D) to form a generally cylindrical body such that the lumen portion 127 and the lumen portion 137 together form a generally cylindrical lumen 107 that is surrounded by the proximal inner surfaces 122 and 132 and the distal inner surfaces 123 and 133.

When the closed segment 120 and the open segment 130 are in an assembled condition, the proximal inner surfaces 122 and 132 together form the interior surface of a generally cylindrical body defining a lumen having a first diameter D1. In the assembled condition, the distal inner surfaces 123 and 133 together form the interior surface of a generally cylindrical extension defining a lumen having a second diameter D2 that is less than the first diameter. In the assembled condition, the body and the extension may be divided into the closed segment 120 and the open segment 130 by a plane extending through a center of the body and the extension in the longitudinal direction.

As shown in FIGS. 2C and 2D, the extension may extend from a distal end of the body (i.e., the shelves 125, 135) to a free end (i.e., the distal edge 126), and the body lumen and the extension lumen may be coaxial with one another. In the assembled condition, the shelves 125 and 135 may together define a ring-shaped shelf having a width W and facing in a direction toward the proximal edges 124 and 134.

As can be seen in FIG. 2A, the alignment feature in the form of the alignment pins 140 may be configured to extend between the closed segment 120 and the open segment 130 to align the closed segment with the open segment in a longitudinal direction X and in a lateral direction Y transverse to the longitudinal direction when the closed and open segments are in an assembled relationship.

Although the outer surfaces 121, 131 of the closed and open segments 120, 130 together form a generally cylindrical outer surface, in other embodiments, the outer surfaces may have any other shape, and the inner surface 114 of the ring preferably has a corresponding shape configured to fit snugly around the outer surfaces 121, 131. Further, while the proximal inner surfaces 122, 132 together define a generally cylindrical surface, in other embodiments, these proximal inner surfaces may define any other shape, such as a cube or prism, although it is preferred that the proximal inner surfaces define a diameter D1 that is greater than the diameter D2 defined by the distal inner surfaces 123, 133.

The diameter D1 defined by the proximal inner surfaces 122 and 132 preferably is greater than the outer diameter D3 (FIG. 3A) of the proximal segment 56 of the sheath 48, and the second D2 defined by the distal inner surfaces 123 and 133 preferably is less than the outer diameter of the proximal segment. This arrangement will enable the proximal segment 56 of the outer sheath 48 to be inserted into the lumen 107 until the distal end 59 of the proximal segment contacts the shelves 125 and 135.

To enable the retaining element 52 of the delivery device 10 to be inserted between the distal inner surfaces 123 and 133, the diameter D2 defined by the distal inner surfaces preferably is greater than the outer diameter D4 (FIG. 3A) of the retaining element. To enable the prosthetic heart valve 70 to be smoothly transferred from the lumen 107 of the assembled loading tool 100 to the lumen of the proximal segment 56, the diameter D2 defined by the distal inner surfaces 123 and 133 preferably is approximately equal to the lumen diameter of the proximal segment. In a preferred embodiment, to keep the proximal segment 56 of the outer sheath 48 longitudinally aligned with the lumen 107 of the assembled loading tool 100, the width W of the shelf is approximately equal to the wall thickness of the proximal segment of the outer sheath.

Figure 3A:
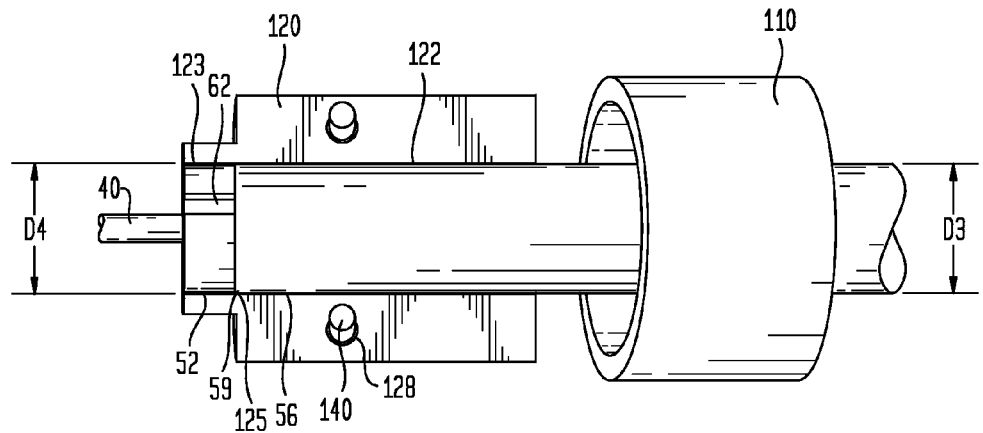
FIG. 3A is a side view of the closed segment and the ring of the loading tool of FIG. 2A disposed around the outer sheath of the delivery device of FIG. 1A.
Figure 3B:
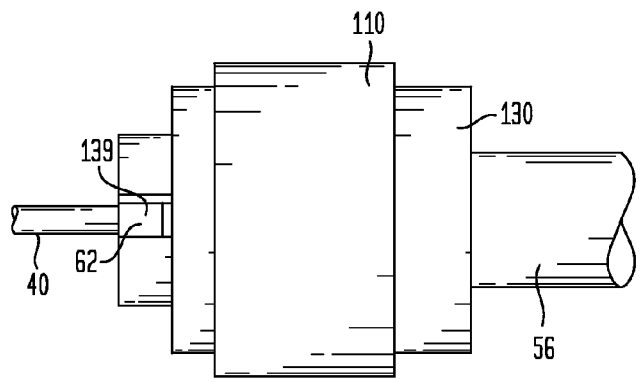
FIG. 3B is a side view of the loading tool of FIG. 2A assembled around the outer sheath of the delivery device of FIG. 1A.
Figure 3C:
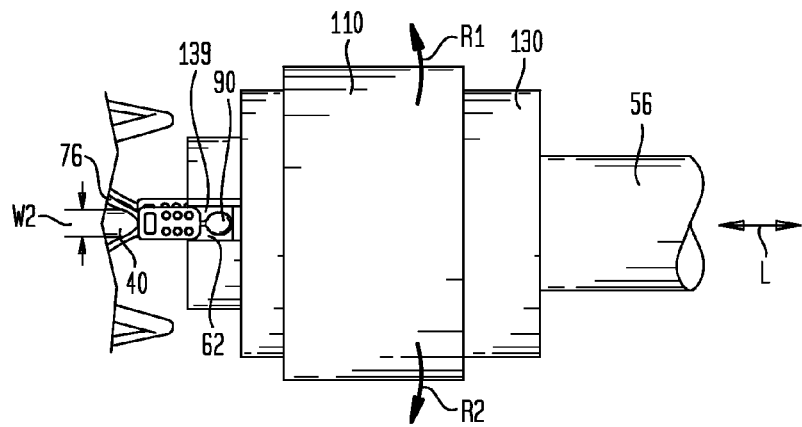
FIG. 3C is a side view of the loading tool of FIG. 2A assembled around the outer sheath of the delivery device of FIG. 1A, with the opening of the open segment aligned with a recess of the retaining element.

FIGS. 3A-3C illustrate steps for using the loading tool 100 to load a prosthetic heart valve 70 into the delivery device 10. For ease of visualization, only the stent 76 is shown being loaded into the delivery device 10, rather than the entire prosthetic heart valve 70.

The proximal segment 56 may be retracted proximally relative to the retaining element 52 until the retaining element is disposed distally of the distal end 59 of the proximal segment. FIG. 3A shows the closed segment 120 assembled around the proximal segment 56 of the outer sheath 48 and around the retaining element 52, with the distal end 59 of the proximal segment abutting the shelf 125. The distal inner surface 123 may be assembled around the retaining element 52. The alignment pins 140 may be assembled in the bores 128.

As shown in FIG. 3B, the open segment 130 may be assembled to the closed segment 120 so that the alignment pins 140 extend into the bores 138. When the open segment 130 is assembled to the closed segment 120, the proximal inner surface 132 (not visible in FIG. 3B) will reside around the proximal segment 56 of the outer sheath 48, such that the distal end 59 of the proximal segment abuts the shelf 135. The distal inner surface 133 (not visible in FIG. 3B) will reside around the retaining element 52.

The ring 110 may be slid over the assembled closed segment 120 and open segment 130, such that the ring removably clamps the closed and open segments against one another. Then, the loading tool 100 may be rotated until the slot 139 of the open segment 130 is circumferentially aligned with a first one of the recesses 62 of the retaining element 52.

As shown in FIG. 3C, a first one of the retainers 90 of the stent 76 may be placed into the first recess 62 of the retaining element 52. Once the first retainer 90 is positioned within a corresponding recess 62, the loading tool 100 may be rotated in either rotational direction R1 or R2 about a longitudinal axis L thereof until the slot 139 is circumferentially aligned with a second one of the recesses 62. A second one of the retainers 90 may then be placed into the second recess 62, after which the loading tool 100 may be rotated in the same rotational direction until the slot 139 is circumferentially aligned with the third one of the recesses 62. The third retainer 90 may be placed into the third recess 62, and the loading tool 100 may be rotated in either rotational direction until the slot 139 is aligned with any of the recesses, as can be seen in FIG. 4A.

To complete the loading of the prosthetic heart valve 70 into the proximal segment 56 of the outer sheath 48, the proximal segment may be advanced distally by a user rotating the knob 36 of the handle assembly 12 (FIG. 1A). Because the distal end 59 of the proximal segment 56 is in contact with the shelves 125 and 135, distal advancement of the proximal segment will push the loading tool 100 distally therewith, thus moving the proximal segment and the loading tool distally relative to the retaining element 52.

Figure 4A:
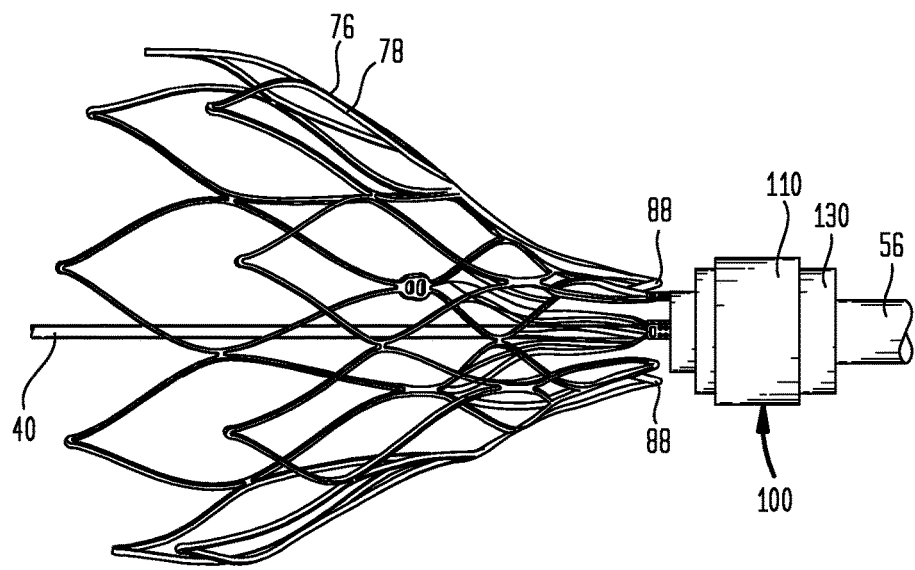
FIG. 4A is a side view of the loading tool of FIG. 2A assembled around the outer sheath of the delivery device of FIG. 1A, with the retainers of a collapsible stent secured in the recesses of the retaining element.
Figure 4B:
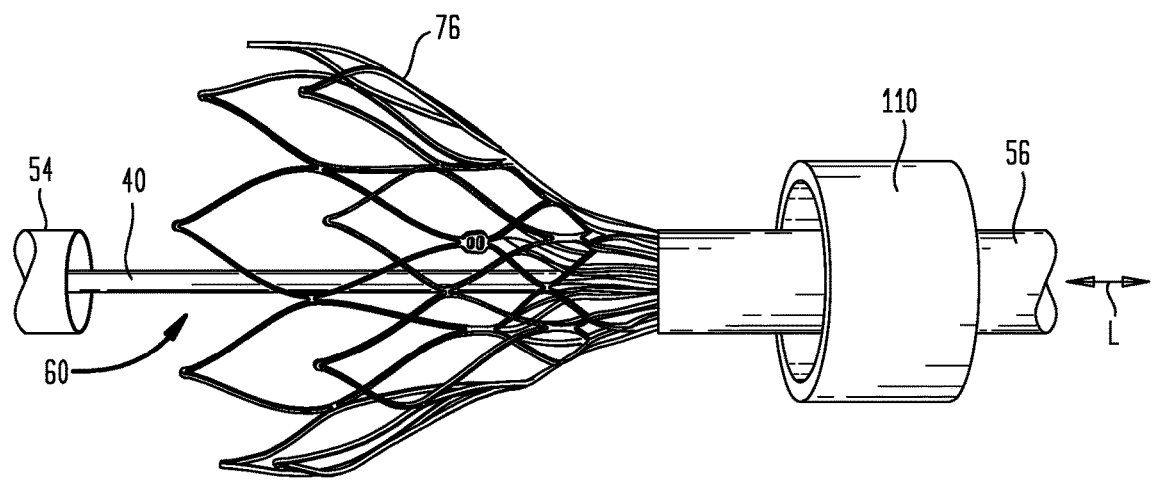
FIG. 4B is a side view of a collapsible stent secured to the delivery device of FIG. 1A.

Once the proximal segment 56 of the outer sheath 48 is distally advanced far enough to cover the recesses 62 of the retaining element 52, as shown in FIG. 4B, the loading tool 100 may be removed from the delivery device 10 by sliding the ring 110 off of the closed segment 120 and the open segment 130 and separating the closed and open segments from one another to remove them from the proximal segment. The remainder of the stent 76 may be compressed into the compartment 60 by continuing to advance the proximal segment 56 distally until the stent is completely covered by the outer sheath 48.

Depending on the particular design of the stent, once the retainers 90 are covered by the proximal segment 56, the junctions 88 of the stent struts 78 that do not have retainers thereon may extend too far radially outward to be captured by the advancing proximal segment, as can be seen, for example, in FIG. 4A. In such a situation, it may be necessary for a user to manually radially compress the junctions 88 that do not have retainers 90 thereon, so they will enter either the loading tool 100 (before removal) or the proximal segment 56 (after removal of the loading tool) as the proximal segment is advanced distally.

In the example shown in FIGS. 3A through 4B, the stent 76 has three retainers 90 and the retaining element 52 of the delivery device 10 has three corresponding recesses 62. However, that need not be the case. The stent 76 may have any number of retainers 90, and the retaining element 52 may have any number of recesses 62, although it is preferable that the number of recesses be equal to or greater than the number of retainers, so that each retainer may be placed into a corresponding recess.

As shown in FIGS. 2A through 4B, the loading tool 100 has a ring 110, separate closed and open segments 120, 130, and separate alignment pins 140. In other embodiments (e.g., FIGS. 4C-4E), other configurations of these components of the loading tool are possible. For example, the ring 110 may be modified or omitted entirely. The ring 110 may take any form that is configured to clamp the closed and open segments 120, 130 to one another in an assembled relationship, such as a string, a rubber band, a pair of tongs, and the like.

The ring 110 and/or the alignment pins 140 may be omitted in embodiments where the closed and open segments 120, 130 can be joined without assistance from removable components. For example, the closed and open segments 120, 130 may have mating features, such as tabs and recesses, that can engaged with one another by sliding the open segment longitudinally relative to the closed segment. Such mating features may also serve to align the closed and open segments 120, 130 so that separate alignment pins 140 are not needed.

In some embodiments, such as the exemplary loading tool 200 described below, the closed and open segments 120, 130 need not be completely separable from one another. For example, the closed and open segments 120, 130 may each have a hinge extending along one longitudinal edge thereof, and the hinge may have a shape memory that biases it towards clamping the closed and open segments against one another, or the hinge may have no shape memory, and a clasp may be provided to hold the closed and open segments against one another in a clamped condition.

Figure 4C:
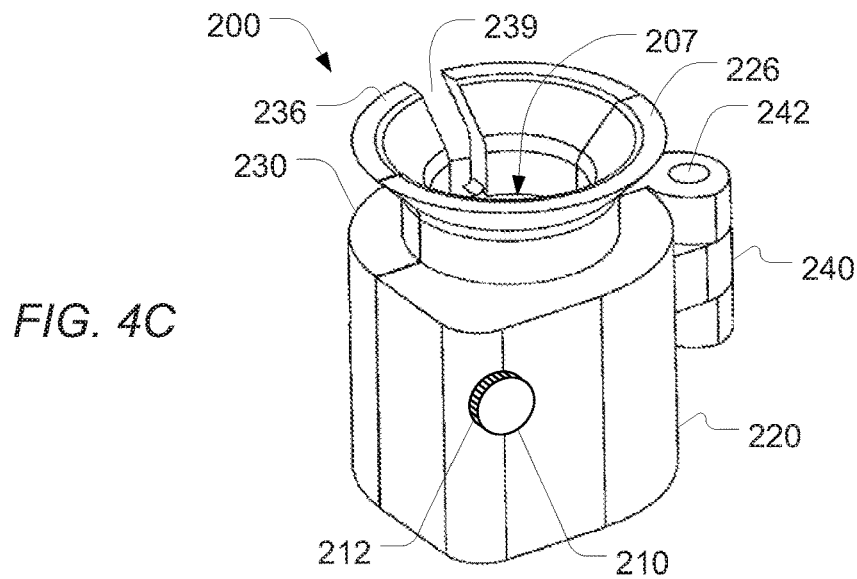
FIG. 4C is a perspective view of another loading tool configured to load the prosthetic heart valve of FIG. 1D into the delivery device of FIG. 1A.
Figure 4D:
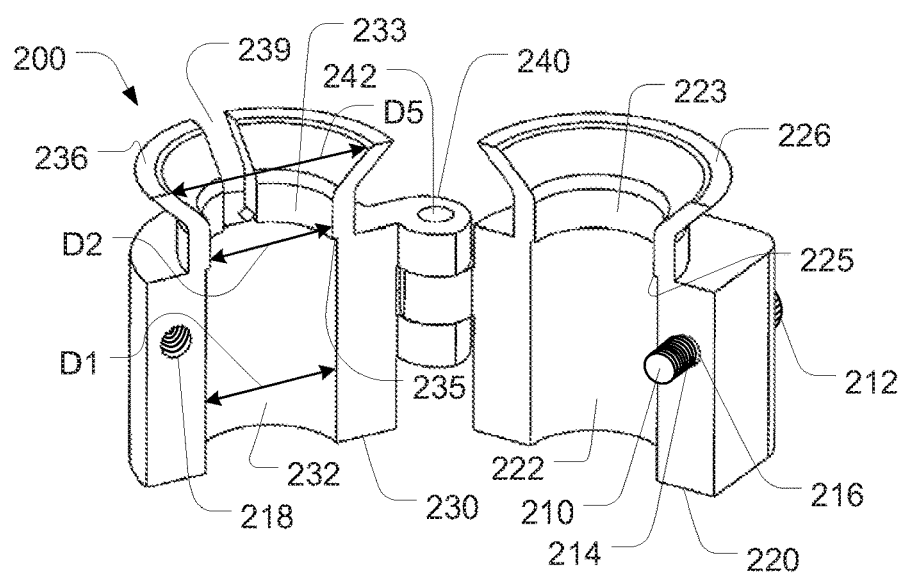
FIG. 4D is an inside perspective view of the loading tool of FIG. 4C shown in an open position.
Figure 4E:
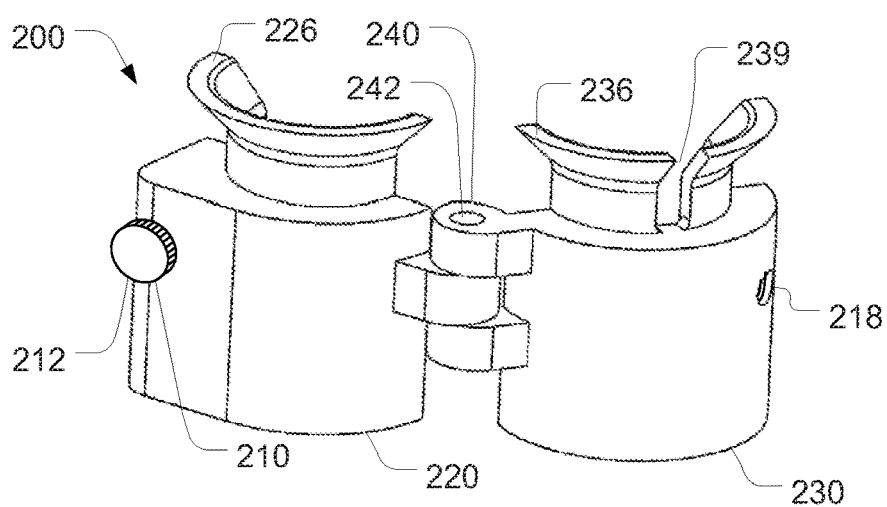
FIG. 4E is an outside perspective view of the loading tool of FIG. 4C shown in an open position.

For example, FIGS. 4C-4E illustrate a loading tool 200 configured to load the prosthetic heart valve 70 into the delivery device 10. The loading tool 200 is a variation of the loading tool 100 of FIGS. 2A-2D. Elements of the loading tool 200 that are not described below should be understood to be the same as the corresponding elements described above with reference to the loading tool 100 shown in FIGS. 2A-2D.

The loading tool 200 includes a clamp in the form of a threaded knob 210, a first segment or closed segment 220 and a second segment or open segment 230 that together form a generally cylindrical body having an extension extending therefrom, and a hinge 240 configured to permit the closed and open segments to pivot relative to one another. As shown in the figures herein, the closed segment 220 and the open segment 230 have identical inner surfaces except that the open segment has an opening in the form of a slot 239 formed therein, which will be described in detail below.

The threaded knob 210 may have a handle portion 212 and a generally cylindrical threaded rod portion 214 extending from the handle portion. The handle portion 212 may be roughened or knurled to provide a surface that can be more easily gripped and rotated by a user. The threaded knob 210 may be configured to clamp the closed segment 220 and the open segment 230 to one another. The threaded rod portion 214 may extend through the closed segment 220 within a generally cylindrical opening 216, and the threaded rod portion may be configured to mate with a generally cylindrical threaded opening 218 that may extend partially through or entirely through the open segment 230. Once the closed segment 220 and the open segment 230 are pivoted into a closed position, the threaded knob 210 can clamp the closed and open segments together by rotating the threaded knob so that the threaded rod portion 214 engages within the threaded opening 218. As shown in FIG. 4C, when the threaded rod portion 214 is engaged within the threaded opening 218, the closed segment 220 and the open segment 230 may remain coupled or clamped to one another during use of the loading tool 200.

As shown in FIGS. 4D and 4E, the closed segment 220 may have a proximal inner surface 222 and a distal inner surface 223, and the open segment 330 may have a proximal inner surface 232 and a distal inner surface 233. A slot 239 may extend between the outer surface and the distal inner surface 233. The slot 239 may have an open side at the distal edge 236 and a closed side opposite the open side and may extend in a direction towards the shelf 235. The slot may have a width greater than a width W2 of the retainers 90 of the prosthetic heart valve 70 (FIG. 3C). The closed segment 220 and the open segment 230 may be assembled to one another (FIG. 4C) to form a generally cylindrical body having a generally cylindrical lumen 207 that is surrounded by the proximal inner surfaces 222 and 232 and the distal inner surfaces 223 and 233.

When the closed segment 220 and the open segment 230 are in a clamped condition, the proximal inner surfaces 222 and 232 together form the interior surface of a generally cylindrical body defining a lumen having a first diameter D1. In the assembled condition, the distal inner surfaces 223 and 233 together form the interior surface of an extension defining a lumen having a generally cylindrical portion having a second diameter D2 that is less than the first diameter, and a generally conical portion widening from the second diameter to a third diameter D5 at the distal edges 226, 236. As shown in FIG. 4D, the third diameter D5 may be greater than the first diameter D1. The generally cylindrical portion of the distal inner surfaces 223, 233 may be disposed adjacent the shelves 225, 235, and the generally conical portion of the distal inner surfaces may be disposed adjacent the distal edges 226, 236.

Compared to the loading tool 100, the generally conical portion of the distal inner surfaces 223, 233 of the loading tool 200 may permit a more gradual funneling (i.e., reduction of radial diameter) of the prosthetic heart valve 70 into the loading tool, which may reduce the bending force experienced by the stent 76 adjacent to the retainers 90 while the retainers are being placed into the recesses 62 of the delivery device 10, and which may reduce the bending force experienced by the prosthetic heart valve as the loading tool is pushed distally over the prosthetic heart valve as described above with reference to FIGS. 4A and 4B.

The hinge 240 of the loading tool 200 may be configured to permit the closed and open segments 220, 230 to pivot relative to one another between the open position shown in FIGS. 4D and 4E and the clamped position shown in FIG. 4C. The hinge 240 may include portions of the closed and open segments 220, 230 alternatingly interleaved with one another. The hinge 240 may include a lumen extending substantially parallel to an extension direction of the lumen 207, and a pin 242 may extend within the lumen to retain the closed and open segments 220, 230 coupled to one another.

In an alternative example, the closed and open segments 220, 230 may be formed as a single unitary component with a living hinge extending therebetween replacing the hinge 240 shown in FIGS. 4C-4E. In another embodiment, the closed and open segments 220, 230 may be formed as a single unitary component from a material that has sufficient elasticity that it can be radially stretched by a user and slid onto the proximal segment 56 from the direction of the distal tip 50 of the delivery device 10, and the material may automatically regain its initial contracted shape when the user releases the unitary component. In another example, the closed and open segments 220, 230 may be formed as a single unitary component from a material that expands when heated and contracts when cooling. Such a material may be heated before the unitary component is slid onto the proximal segment 56, and the material may automatically regain its initial contracted shape when the heat dissipates.

As shown and described in FIGS. 1A through 4E, the delivery device 10 is configured to retain and deliver a collapsible prosthetic mitral valve 70 into the native mitral annulus of a patient, and the loading tools 100 and 200 are configured to load such prosthetic mitral valve into the delivery device. However, the loading tools 100 and 200 may be used to load any collapsible valve or any collapsible stent having retainers into any delivery device having recesses distributed in a circumferential direction about a longitudinal axis of the delivery device. For example, the loading tools 100 and 200 may be used to load a collapsible prosthetic aortic valve into a transfemoral or transapical aortic valve delivery device, such as those shown and described in co-owned and co-pending U.S. Patent Application Publication No. 2013/0297011, the disclosure of which is hereby incorporated herein by reference.

Figure 5A:
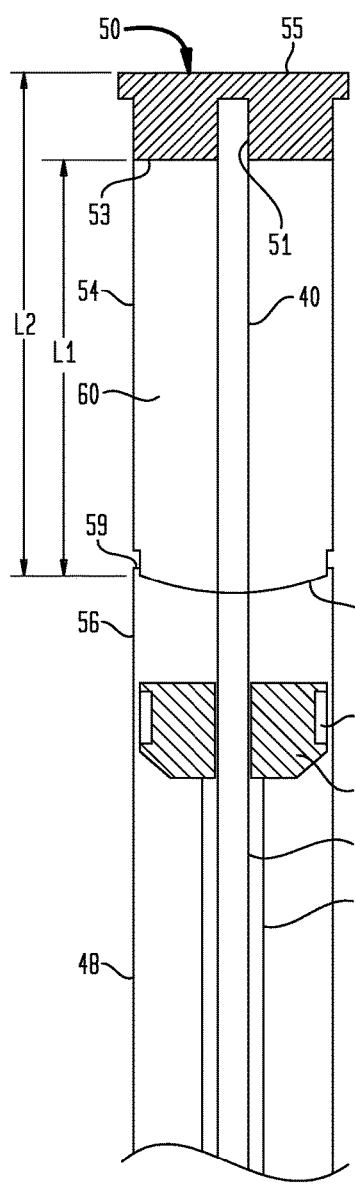
FIG. 5A is a schematic longitudinal cross-section of a distal portion of the delivery device of FIG. 1A.

FIG. 5A shows a cross-section of the distal portion of the delivery device 10 described above with reference to FIG. 1A. The distal end of the inner shaft 40 of the catheter assembly 16 is affixed to a recess 51 within the distal tip, and the distal segment 54 of the outer sheath 48 is affixed to the distal tip 50, so that the distal tip and the distal segment move together when the inner shaft moves. The distal tip 50 has a proximal surface 53 that is located a distance L1 from the proximal end 58 of the distal segment, which is less than a distance L2 between the distal surface 55 of the distal tip and the proximal end of the distal segment.

As mentioned above, during transapical mitral valve delivery, for example, there may be relatively little working space for the distal segment 54 to move in a distal direction. If the distal segment 54 moves too far distally during deployment of a prosthetic heart valve from the delivery device 10, the distal tip 50 may damage tissue in the left atrium.

Figure 5B:
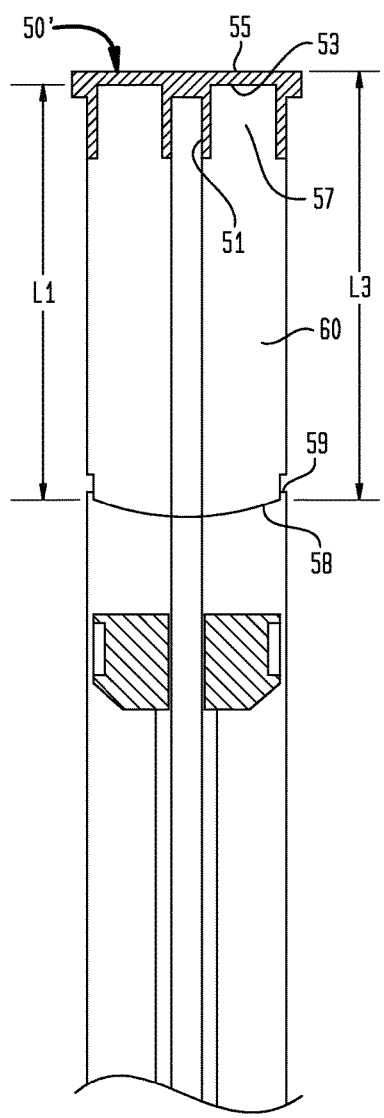
FIG. 5B is a schematic longitudinal cross-section of a variation of the distal portion of the delivery device of FIG. 1A according to another embodiment.

FIG. 5B shows a cross-section of a variation of the distal portion of the delivery device 10 shown in FIG. 5A. The distal tip 50 of FIG. 5A is replaced with a distal tip 50'. The distal tip 50' has an internal recess 57 therein, such that an end surface 53 of the recess is located a distance L1 from the proximal end 58 of the distal segment 54.

Due to the presence of the internal recess 57, the distance L3 between the distal surface 55 of the distal tip 50' and the proximal end 58 of the distal segment 54 may be less than the distance L2 shown in FIG. 5A, while the distance L1 between the proximal surface 53 of the distal tip and the proximal end of the distal segment is the same between the two embodiments. In other words, the length of the compartment 60 is the same between FIGS. 5A and 5B to accommodate the prosthetic heart valve 70, but the length of the catheter assembly 16 may be shorter in the embodiment of FIG. 5B because of the presence of the recess 57. Therefore, the distal tip 50' of FIG. 5B may permit the delivery device 10 to be used to replace a mitral valve in patients having less working space in the left atrium.

Figure 6:
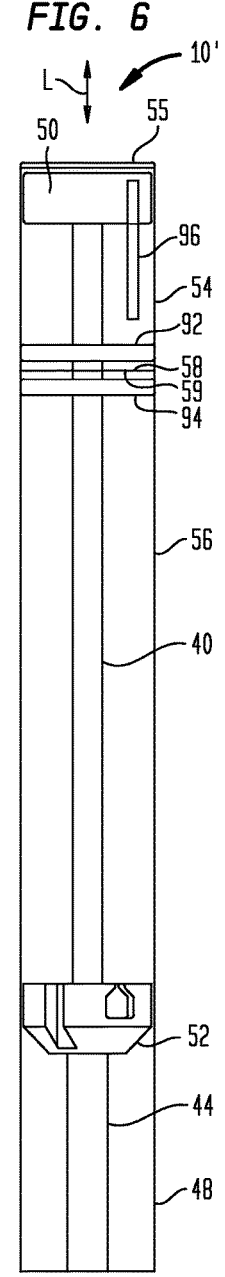
FIG. 6 is a schematic side view of a variation of the distal portion of the delivery device of FIG. 1A showing the outer sheath as partially transparent with marker bands thereon.

FIG. 6 shows a variation of the distal portion of the delivery device 10 shown in FIG. 1A having radiopaque marker bands thereon. As shown in FIG. 6, the delivery device 10' has a distal marker band 92 disposed adjacent the proximal end 58 of the distal segment 54 of the outer sheath 48, and a proximal marker band 94 disposed adjacent the distal end 59 of the proximal segment 56 of the outer sheath. The delivery device 10' also has a longitudinal marker band 96 extending in a direction generally parallel to the longitudinal axis L of the outer sheath 48. A particular delivery device 10' may include any one, two, or all three of the marker bands 92, 94, and 96 as desired. Also, a plurality of marker bands 92, 94, or 96 may be used adjacent to one another. For example, a particular delivery device may include two circumferentially-extending marker bands 92, a first one disposed adjacent the proximal end 58 of the distal segment 54, and a second one disposed adjacent the first one.

The marker bands 92, 94, and 96 may be made of one or more radiopaque materials, such that each marker band may have enhanced visibility to a user under fluoroscopy compared to the material immediately adjacent the marker band. Any suitable radiopaque material may be used for the marker bands, including, for example, metals, ceramics, or thermoplastics.

Each of the marker bands 92 and 94 may include a single band wrapped continuously around the outer sheath 48 in the circumferential direction, or they each may include one or more band portions each extending partially around the outer sheath in the circumferential direction, with gaps between adjacent band portions. The marker band 96 may include a single strip extending most of the distance between the distal tip 50 and the proximal end 58 of the distal segment 54, or it may include one or more spaced band portions that collectively define a band extending in a direction parallel to the longitudinal axis L.

It will be appreciated that the various dependent claims and the features set forth therein can be combined in different ways than presented in the initial claims. For example, any type of distal dip described herein may be included in any delivery device described herein. It will be appreciated that any of the features described in connection with individual embodiments may be shared with others of the described embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In summary, the disclosure herein recites multiple embodiments to summarize the foregoing. Described herein is a loading tool for loading a collapsible prosthetic heart valve into a delivery device. The loading tool may include a body extending in a longitudinal direction between a proximal end and a distal end, the body including a lumen extending between the proximal end and the distal end, the body lumen having a first diameter. The loading tool may also include an extension on the distal end of the body, the extension having a free end and a lumen coaxial with the body lumen, the extension lumen having a second diameter less than the first diameter so as to define a shelf surface between the proximal end of the body and the free end of the extension. The loading tool may further include a slot extending through the extension from the free end toward the distal end of the body; and/or the body and the extension may be divided into separate first and second segments by a plane extending through a center of the body and the extension in the longitudinal direction, and the loading tool may further include a clamp for holding the first and second segments in an assembled relationship; and/or the first and second segments in the assembled relationship may have a maximum outer diameter, and the clamp may be a ring having an interior diameter that is slightly larger than the maximum outer diameter; and/or the first and second segments may be coupled to one another by a hinge, and the clamp may be a threaded knob that is configured to engage with a threaded opening extending within at least one of the first and second segments; and/or the loading tool may further include an alignment feature configured to extend between the first and second segments to align the first segment with the second segment in the longitudinal direction and in a direction transverse to the longitudinal direction when the first and second segments are in the assembled relationship; and/or the extension lumen may have a third diameter at the free end of the extension greater than the second diameter, and at least a portion of the extension lumen can be a conical portion widening from the second diameter to the third diameter.

Also described herein is medical combination. The medical combination may include a delivery device for a collapsible prosthetic heart valve. The delivery device may include an inner sheath elongated along a longitudinal axis. The delivery device may also include an outer sheath at least partially surrounding the inner sheath and slidable relative to the inner sheath along the longitudinal axis, the outer sheath having a first diameter. The delivery device may further include a retaining element affixed to the inner sheath, the retaining element having a plurality of recesses distributed circumferentially around its perimeter, each recess being configured to accept a corresponding retainer of the prosthetic heart valve, the perimeter of the retaining element having a second diameter.

The medical combination may also include a loading tool for loading the collapsible prosthetic heart valve into the delivery device. The loading tool may include a body extending in a longitudinal direction between a proximal end and a distal end, the body including a lumen extending between the proximal end and the distal end, the body lumen having a third diameter greater than the first diameter so that the outer sheath fits within the body lumen when the loading tool is in an assembled condition around the delivery device.

The loading tool may also include an extension on the distal end of the body, the extension having a free end and a lumen coaxial with the body lumen, the extension lumen having a fourth diameter less than the third diameter so as to define a shelf surface between the proximal end of the body and the free end of the extension, the fourth diameter being greater than the second diameter so that the retaining element fits within the extension lumen when the loading tool is the assembled condition around the delivery device. The loading tool may further include a slot extending through the extension from the free end toward the distal end of the body; and/or the body and the extension may be divided into separate first and second segments by a plane extending through a center of the body and the extension in the longitudinal direction, and the loading tool may further include a clamp for holding the first and second segments in an assembled relationship; and/or the first and second segments in the assembled relationship may have a maximum outer diameter, and the clamp may be a ring having an interior diameter that is slightly larger than the maximum outer diameter; and/or the first and second segments may be coupled to one another by a hinge, and the clamp may be a threaded knob that is configured to engage with a threaded opening extending within at least one of the first and second segments; and/or the medical combination may also include an alignment feature configured to extend between the first and second segments to align the first segment with the second segment in the longitudinal direction and in a direction transverse to the longitudinal direction when the first and second segments are in the assembled relationship; and/or the extension lumen may have a third diameter at the free end of the extension greater than the second diameter, and at least a portion of the extension lumen may be a conical portion widening from the second diameter to the third diameter; and/or the medical combination may also include the prosthetic heart valve having the retainers, the recesses of the retaining element of the delivery device being equal in number to the retainers of the prosthetic heart valve; and/or the delivery device may further include an inner shaft at least partially surrounded by the inner sheath and the outer sheath and slidable relative to the inner sheath and the outer sheath along the longitudinal axis, the outer sheath may include a proximal segment and a distal segment that together define a compartment sized to receive the prosthetic heart valve therein, and the distal segment may be affixed to the inner shaft.

Also described herein is a method of loading a collapsible prosthetic heart valve into a delivery system. The method may include assembling a loading tool around a distal end of a delivery device for a collapsible prosthetic heart valve. The delivery device may have a retaining element and an outer sheath elongated along a longitudinal axis and slidable relative to the retaining element along the longitudinal axis, the retaining element having a plurality of recesses distributed circumferentially around its perimeter.

The loading tool may have a body and an extension on the distal end of the body, the body extending in a longitudinal direction between a proximal end and a distal end and including a lumen extending between the proximal end and the distal end, the extension having a free end and a lumen coaxial with the body lumen, the extension lumen defining a shelf surface between the proximal end of the body and the free end of the extension, the loading tool having a slot extending through the extension from the free end toward the distal end of the body.

The method may also include placing a first retainer of a collapsible prosthetic heart valve through the slot and into a corresponding first one of the recesses of the retaining element, and rotating the loading tool about the longitudinal axis until a second one of the recesses of the retaining element is exposed within the slot. The method may further include placing a second retainer of the collapsible prosthetic heart valve through the slot and into a corresponding second one of the recesses of the retaining element, and rotating the loading tool about the longitudinal axis until the first one and the second one of the recesses are not exposed within the slot. The method may also include advancing the outer sheath relative to the retaining element along the longitudinal axis, so that the outer sheath covers the first one and the second one of the recesses, and removing the loading tool from the distal end of the delivery device; and/or the body and the extension may be divided into separate first and second segments by a plane extending through a center of the body and the extension in the longitudinal direction, and the assembling step may include assembling the first and second segments around the distal end of the delivery device and removably clamping the first and second segments to one another; and/or the first and second segments in the assembled relationship may define an outer surface, and the clamping step may include sliding a ring around the outer surface; and/or the first and second segments may be coupled to one another by a hinge, and the clamping step may include engaging a threaded knob into a threaded opening extending within at least one of the first and second segments; and/or the clamping step may include aligning an alignment feature extending between the first and second segments to align the first segment with the second segment in the longitudinal direction and in a direction transverse to the longitudinal direction; and/or the assembling step may include positioning the shelf surface abutting a distal end of the outer sheath.

Also described herein is a delivery device for a collapsible prosthetic heart valve. The delivery device may include an inner shaft elongated along a longitudinal axis, and an inner sheath at least partially surrounding the inner shaft and slidable relative to the inner sheath along the longitudinal axis. The delivery device may also include a retaining element affixed to the inner sheath, the retaining element having a plurality of recesses distributed circumferentially around its perimeter, each recess being configured to accept a corresponding retainer of the prosthetic heart valve.

The delivery device may further include an outer sheath including a proximal segment and a distal segment that together define a compartment sized to receive the prosthetic heart valve therein, each of the proximal segment and the distal segment being independently slidable relative to the retaining element along the longitudinal axis. The delivery device may also include an atraumatic tip affixed to a distal end of the distal segment, the atraumatic tip having a distal end, a proximal end, and a recess open towards an interior of the distal segment, the recess sized to receive an end of the prosthetic heart valve therein in a collapsed condition.

Also described herein is another delivery device for a collapsible prosthetic heart valve. The delivery device may include an inner shaft extending in a longitudinal direction, and an inner sheath at least partially surrounding the inner sheath and slidable relative to the inner sheath in the longitudinal direction. The delivery device may also include a retaining element affixed to the inner sheath, the retaining element having a plurality of recesses distributed circumferentially around its perimeter, each recess being configured to accept a corresponding retainer of the prosthetic heart valve.

The delivery device may further include an outer sheath including a proximal segment and a distal segment that together define a compartment sized to receive the prosthetic heart valve therein, each of the proximal segment and the distal segment being independently slidable relative to the retaining element in the longitudinal direction, and a radiopaque marker on at least one of the proximal segment and the distal segment; and/or the proximal segment may have a distal end abutting a proximal end of the distal segment in a closed condition of the outer sheath, and a first radiopaque marker may extend in a circumferential direction adjacent the distal end of the proximal segment or adjacent the proximal end of the distal segment; and/or the first radiopaque marker may extend in the circumferential direction adjacent the distal end of the proximal segment, and a second radiopaque marker may extend in the circumferential direction adjacent the proximal end of the distal segment; and/or the radiopaque marker may extend in the longitudinal direction on the distal segment.

The invention claimed is:

1. A medical combination, comprising:
a delivery device for a collapsible prosthetic heart valve, the delivery device including:
an inner sheath elongated along a longitudinal axis;
an outer sheath at least partially surrounding the inner sheath and slidable relative to the inner sheath along the longitudinal axis, the outer sheath having a first diameter; and
a retaining element affixed to the inner sheath, the retaining element having a plurality of recesses distributed circumferentially around its perimeter, each recess being configured to accept a corresponding retainer of the prosthetic heart valve, the perimeter of the retaining element having a second diameter; and a loading tool for loading the collapsible prosthetic heart valve into the delivery device, the loading tool including:
  a body extending in a longitudinal direction between a proximal end and a distal end, the body including a lumen extending between the proximal end and the distal end, the body lumen having a third diameter greater than the first diameter so that the outer sheath fits within the body lumen when the loading tool is in an assembled condition around the delivery device;
  an extension on the distal end of the body, the extension having a free end and a lumen coaxial with the body lumen, the extension lumen having a fourth diameter less than the third diameter so as to define a shelf surface between the proximal end of the body and the free end of the extension, the fourth diameter being greater than the second diameter so that the retaining element fits within the extension lumen when the loading tool is the assembled condition around the delivery device, the shelf surface facing in a direction toward the proximal end of the body and having a width that is approximately equal to a wall thickness of the outer sheath; and
  a slot extending through the extension from the free end toward the distal end of the body.

2. The medical combination as claimed in claim 1, wherein the body and the extension are divided into separate first and second segments by a plane extending through a center of the body and the extension in the longitudinal direction, and the loading tool further includes a clamp for holding the first and second segments in an assembled relationship.

3. The medical combination as claimed in claim 2, wherein the first and second segments in the assembled relationship have a maximum outer diameter, and the clamp is a ring having an interior diameter that is slightly larger than the maximum outer diameter.

4. The medical combination as claimed in claim 2, wherein the first and second segments are coupled to one another by a hinge, and the clamp is a threaded knob that is configured to engage with a threaded opening extending within at least one of the first and second segments.

5. The medical combination as claimed in claim 2, further comprising an alignment feature configured to extend between the first and second segments to align the first segment with the second segment in the longitudinal direction and in a direction transverse to the longitudinal direction when the first and second segments are in the assembled relationship.

6. The medical combination as claimed in claim 1, wherein the extension lumen has a fifth diameter at the free end of the extension greater than the fourth diameter, and at least a portion of the extension lumen is a conical portion widening from the fourth diameter to the fifth diameter.

7. The medical combination as claimed in claim 1, further comprising the prosthetic heart valve having the retainers, the recesses of the retaining element of the delivery device being equal in number to the retainers of the prosthetic heart valve.

8. The medical combination as claimed in claim 1, wherein the delivery device further comprises an inner shaft at least partially surrounded by the inner sheath and the outer sheath and slidable relative to the inner sheath and the outer sheath along the longitudinal axis, the outer sheath comprises a proximal segment and a distal segment that together define a compartment sized to receive the prosthetic heart valve therein, and the distal segment is affixed to the inner shaft.

9. The medical combination as claimed in claim 1, wherein the slot has an open side at the distal end of the body and a closed side opposite the open side.

10. The medical combination as claimed in claim 9, wherein the slot has a width greater than a width of each of the retainers of the prosthetic heart valve.

11. The medical combination as claimed in claim 1, further comprising:
  the prosthetic heart valve, the outer sheath defining a compartment configured to receive the prosthetic heart valve therein, and the body lumen and the extension lumen being configured to receive the prosthetic heart valve therethrough.

* * * * *